United States Patent [19]

Ackermann et al.

[11] 4,225,616
[45] Sep. 30, 1980

[54] TETRAHALOETHYLCYCLOPROPANE-CARBOXYLIC ACID ESTERS

[75] Inventors: Peter Ackermann, Reinach; Jozef Drabek, Oberwil; Saleem Farooq, Ettingen; Laurenz Gsell, Basel; Odd Kristiansen, Mohlin; Rudolf Wehrli, Rheinfelden, all of Switzerland

[73] Assignee: Ciba-Geigy Corporation, Ardsley, N.Y.

[21] Appl. No.: 50,562

[22] Filed: Jun. 21, 1979

[30] Foreign Application Priority Data

Jun. 26, 1978 [CH] Switzerland .................. 6936/78
May 21, 1979 [CH] Switzerland .................. 4741/79

[51] Int. Cl.$^3$ .................. C07C 69/74; A01N 53/00
[52] U.S. Cl. .................. 424/305; 260/340.5 R; 424/282; 560/124
[58] Field of Search .................. 560/124; 424/305, 282; 260/340.5 R

[56] References Cited

U.S. PATENT DOCUMENTS

| | | | |
|---|---|---|---|
| 3,954,814 | 5/1976 | Mizutani | 560/124 |
| 3,981,903 | 9/1976 | Hirano | 560/124 |
| 4,003,945 | 1/1977 | Kitamura | 560/124 |

*Primary Examiner*—Natalie Trousof
*Assistant Examiner*—Michael Shippen
*Attorney, Agent, or Firm*—John J. Maitner

[57] ABSTRACT

Cyclopropanecarboxylic acid esters of the formula

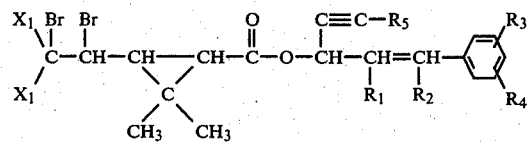

in which $X_1$ is fluorine, chlorine or bromine, $R_1$ and $R_2$ are each hydrogen, fluorine, chlorine, bromine or methyl, $R_3$ and $R_4$ are each hydrogen, fluorine, chlorine, bromine, methyl, methoxy, nitro or dimethylamine, or together are methylenedioxy, and $R_5$ is hydrogen or methyl, processes for producing them, and their use in controlling insect pests.

10 Claims, No Drawings

TETRAHALOETHYLCYCLOPROPANE-CARBOXYLIC ACID ESTERS

The present invention relates to cyclopropanecarboxylic acid esters, to processes for producing them, and to their use in controlling insect pests.

The cyclopropanecarboxylic acid esters have the formula $$\underset{X_1}{\overset{X_1}{\diagdown}}\underset{Br}{\overset{Br}{\underset{|}{C}}}-CH-CH\underset{\underset{CH_3}{\diagup}\underset{CH_3}{\diagdown}}{\overset{}{\diagdown C\diagup}}CH-\overset{O}{\overset{\|}{C}}-O-\underset{R_1}{\overset{}{\underset{|}{CH}}}-\underset{R_2}{\overset{C\equiv C-R_5}{\underset{|}{C}}}=C-\underset{R_4}{\overset{R_3}{\diagup\diagdown}}\quad(I)$$

in which
- $X_1$ is fluorine, chlorine or bromine,
- $R_1$ and $R_2$ are each hydrogen, fluorine, chlorine, bromine or methyl,
- $R_3$ and $R_4$ are each hydrogen, fluorine, chlorine, bromine, methyl, methoxy, nitro or dimethylamine, or together are methylenedioxy, and
- $R_5$ is hydrogen or methyl.

Compounds of the formula I which are preferred on account of their action are those wherein
- $X_1$ is chlorine or bromine,
- $R_1$ is hydrogen, chlorine, bromine or methyl,
- $R_2$ is hydrogen,
- $R_3$ is hydrogen, chlorine, bromine, nitro or dimethylamine,
- $R_4$ is hydrogen, and
- $R_5$ is hydrogen or methyl.

Of particular importance however are compounds of the formula I wherein
- $X_1$ is chlorine,
- $R_1$ is hydrogen, chlorine or bromine, and
- $R_2$, $R_3$, $R_4$ and $R_5$ are each hydrogen.

The compounds of the formula I are produced by methods known per se, for example as follows:

(II) $\quad X_1\diagdown C(Br)(X_1)-CH-CH-C(CH_3)_2-CH-C(=O)-OH$ +

(III) $\quad X-CH(C\equiv C-R_5)-C(R_1)=C(R_2)-C_6H_3(R_3)(R_4)$ $\xrightarrow{\text{acid-binding agent}}$ I $\quad$ (1)

(IV) $\quad X_1\diagdown C(Br)(X_1)-CH-CH-C(CH_3)_2-CH-C(=O)-X$ +

(V) $\quad HO-CH(C\equiv C-R_5)-C(R_1)=C(R_2)-C_6H_3(R_3)(R_4)$ $\xrightarrow{\text{acid-binding agent}}$ I $\quad$ (2)

(II) + (V) $\xrightarrow{\text{water-binding agent}}$ I $\quad$ (3)

(VI) $\quad X_1\diagdown C(Br)(X_1)-CH-CH-C(CH_3)_2-CH-COOR$ +

(V) $\xrightarrow{-ROH}$ I $\quad$ (4)

(VII) $\quad X_1\diagup C=CH-CH-C(CH_3)_2-CH-COO-CH(C\equiv C-R_5)-C(R_1)=C(R_2)-C_6H_3(R_3)(R_4)$ $\xrightarrow{\text{bromination}}$ I $\quad$ (5)

In the formulae II to VII, the symbols $X_1$ and $R_1$ to $R_5$ have the meanings given for the formula I.

In the formulae III and IV, X is a halogen atom, particularly chlorine or bromine, and in the formula VI R is $C_1$–$C_4$-alkyl, especially methyl or ethyl. Suitable acid-binding agents for the processes 1 and 2 are in particular tertiary amines, such as trialkylamine and pyridine, also hydroxides, oxides, carbonates and bicarbonates of alkali metals and alkaline-earth metals, and also alkali metal alcoholates, for example potassium tertbutylate and sodium methylate. As a water-binding agent for the process 3, it is possible to use for example dicyclohexylcarbodiimide. The processes 1 to 4 are performed at a reaction temperature of between −10° and 120° C., usually between 20° and 80° C., under normal or elevated pressure, and preferably in an inert solvent or diluent. Suitable solvents or diluents are for example: ethers and ethereal compounds, such as diethyl ether, dipropyl ether, dioxane, dimethoxyethane and tetrahydrofuran; amides such as N,N-dialkylated carboxylic acid amides; aliphatic, aromatic and also halogenated hydrocarbons, particularly benzene, toluene, xylenes, chloroform and chlorobenzene; nitriles such as acetonitrile; dimethyl sulfoxide, and ketones such as acetone and methyl ethyl ketone.

The starting materials of the formulae II to VII are known, or they can be produced by methods analogous to known methods.

Unless homogeneous optically active starting materials are used in the production process, the compounds of the formula I are obtained as mixtures of various optically active isomers. The different isomeric mixtures can be separated by known methods into the individual isomers. By the term 'compound of the formula I' are meant both the individual isomers and mixtures thereof.

The compounds of the formula I are suitable for controlling various animal and plant pests. They are suitable in particular for controlling insects and phytopathogenic mites and ticks, for example of the orders Lepidoptera, Coleoptera, Homoptera, Heteroptera, Diptera, Acarina, Thysanoptera, Orthoptera, Anoplura, Siphonoptera, Mallophaga, Thysanura, Isoptera, Psocoptera and Hymenoptera.

Compounds of the formula I are especially suitable for controlling insects which damage plants, particularly insects which damage plants by eating, in crops of ornamental plants and useful plants, especially in cotton crops (for example against Spodoptera littoralis and Heliothis virescens), and in crops of vegetables (for example against Leptinotarsa decemlineata and Myzus persicae). The active substances of the formula I also exhibit a very favourable action against flies, such as Musca domestica, and against mosquito larvae.

The acaricidal and insecticidal action can be substantially broadened and adapted to suit given circumstances by the addition of other insecticides and/or acaricides. Suitable additives are for example: organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances which have a synergistic or intensifying effect on pyrethroids. Examples of compounds of this kind are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfonyl)-propyl)-benzene.

Compounds of the formula I surprisingly have an insecticidal spectrum of activity broader than that of chemically analogous compounds known from the German Offenlegungsschrift No. 2,742,546.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations
   dusts, scattering agents, granules (coated granules, impregnated granules and homogeneous granules);
liquid preparations
   (a) water-dispersible concentrates of active substance:wettable powders, pastes or emulsions;
   (b) solutions.

The content of active substance in the compositions described above is between 0.1 and 95%; it is to be mentioned in this respect that with application from an aeroplane, or from other suitable devises, concentrations of up to 99.5% or even the pure active substance can be used.

The active substances of the formula I can be formulated for example as follows (parts are by weight).

Dusts

The following substances are used to produce (a) a 5% dust and (b) a 2% dust:

(a) 5 parts of active substance, and 95 parts of talcum; and (b) 2 parts of active substance, 1 part of highly dispersed silicic acid, and 97 parts of talcum.

The active substance is mixed and ground with the carriers.

Granulate

The following ingredients are used to produce a 5% granulate:

5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a) 40 parts of active substance, 5 parts of sodium lignin sulfonate, 1 part of sodium dibutyl-naphthalene sulfonate, and 54 parts of silicic acid;

(b) 25 parts of active substance, 4.5 parts of calcium lignin sulfonate, 1.9 parts of Champagne chalk/hydroxyethyl cellulose mixture (1:1), 1.5 parts of sodium dibutyl-naphthalene sulfonate, 19.5 parts of silicic acid, 19.5 parts of Champagne chalk, and 28.1 parts of kaolin;

(c) 25 parts of active substance, 2.5 parts of isooctylphenoxy-polyoxyethyleneethanol, 1.7 parts of Champagen chalk/hydroxyethyl cellulose mixture (1:1), 8.3 parts of sodium aluminium silicate, 16.5 parts of kieselguhr, and 46 parts of kaolin; and (d) 10 parts of active substance, 3 parts of a mixture of the sodium salts of saturated fatty alcohol sulfates, 5 parts of naphthalenesulfonic acid/formaldehyde condensate, and 82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:
(a) 10 parts of active substance, 3.4 parts of epoxidised vegetable oil, 3.4 parts of a combination emulsifier consisting of fatty alcohol polyglycol ether and alkylarylsulfonate calcium salt, 40 parts of dimethylformamide, and 43.2 parts of xylene;
(b) 25 parts of active substance, 2.5 parts of epoxidised vegetable oil, 10 parts of alkylarylsulfonate/fatty alcohol polyglycol ether mixture, 5 parts of dimethylformamide, and 57.5 parts of xylene; and
(c) 50 parts of active substance, 4.2 parts of tributylphenol-polyglycol ether, 5.8 parts of calcium-dodecylbenzenesulfonate, 20 parts of cyclohexanone, and 20 parts of xylene.

Emulsions of the required concentration can be prepared from these concentrates by dilution with water.

Sprays

The following constituents are used to produce (a) a 5% spray and (b) a 95% spray:
(a) 5 parts of active substance, 1 part of epichlorohydrin, and 94 parts of ligroin (boiling limites 160°–190° C.); and
(b) 95 parts of active substance, and 5 parts of epichlorohydrin.

The invention is further illustrated by the Examples which follow.

EXAMPLE 1

Production of α-ethynyl-γ-phenylallyl-2′,2′-dimethyl-3′-(1″,2″-dibromo-2″,2″-dichloroethyl)-cyclopropanecarboxylic acid ester A solution of 7.64 g of 2,2-dimethyl-3-(1′,2′-dibromo2′,2′-dichloroethyl)-cyclopropanecarboxylic acid chloride in 50 ml of toluene is cooled at 0° C. To this solution is added dropwise 3 ml of pyridine dissolved in 5 ml of toluene, and subsequently 3.16 g of α-ethynyl-γ-phenylallyl alcohol dissolved in 20 ml of toluene. After 20 hours' stirring at room temperature, the reaction mixture is poured into ice-water/hexane. The organic phase is washed with a 10% sodium carbonate solution and a saturated sodium chloride solution, and dried over magnesium sulfate. After the solvent has been distilled off, the crude product is chromatographed through silica gel with ethyl acetate/hexane (1:4) as the eluant. There is thus obtained the compound of the formula

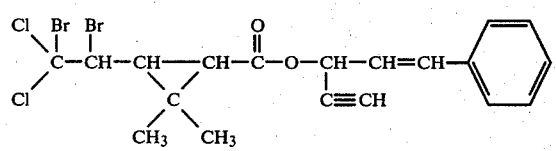

having a refractive index of $n_D^{20°} = 1.5675$.

The following compounds are produced in an analogous manner:

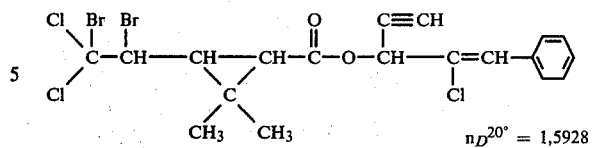

$n_D^{20°} = 1,5928$

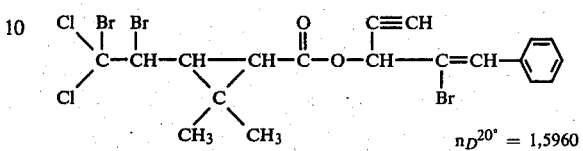

$n_D^{20°} = 1,5960$

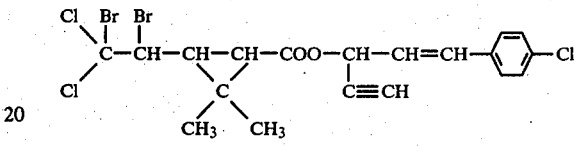

NMR (60 MHz) in CDCl$_3$ in ppm
1,12–1,54 (m, 6H); 1,64–2,75
(m, 3H); 4,42 (t, 0,7H); 5,3
(m, 0,3H); 5,95–7,28 (m, 3H);
7,35 (s, 4H) cis/trans.

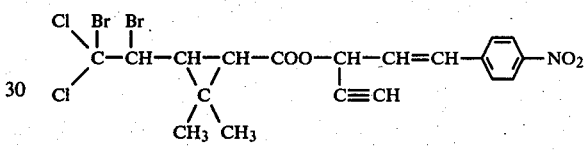

1,28–1,62 (m, 6H); 1,62–2,85
(m, 3H); 4,45 (t, 0,74H); 5,3
(m, 0,3); 6,08–7,4 (m, 3H); 7,6
(d, 2H); 8,3 (d,2H). cis/trans.

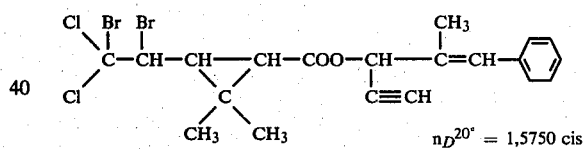

$n_D^{20°} = 1,5750$ cis

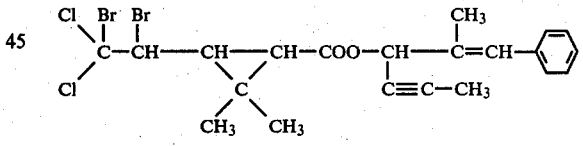

1,08–1,48 (m, 6H); 1,48–2,6
(m, 8H); 4,62–6,32 (m, 3H); 7,3
(s, 5H) cis.

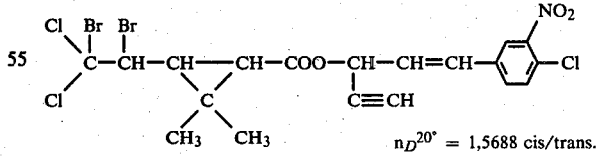

$n_D^{20°} = 1,5688$ cis/trans.

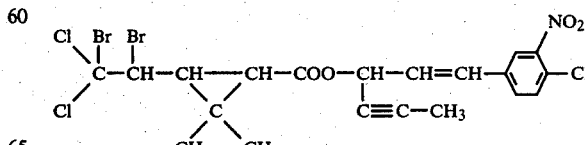

1,08–1,69 (m, 6H); 1,69–2,85
(m, 5H); 5,34 (m, 1H); 5,96–7,22
(m, 3H); 7,5–8,2 (m, 3H) cis.

-continued

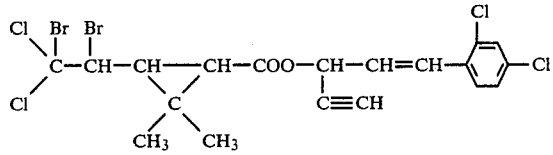

1,35 (m, 6H); 1,85-2,85 (m, 3H); 5,32 (m, 1H); 6,05-7,05 (m, 3H); 7,05-7,6 (m, 3H). cis

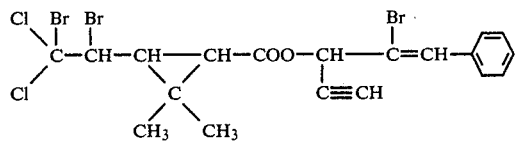

1,38 (m, 6H); 1,78-2,35 (m,2H); 2,72 (m, 1H); 5,2 (m, 1H); 6,25 (m, 1H); 7,0-7,8 (m, 5H) cis.

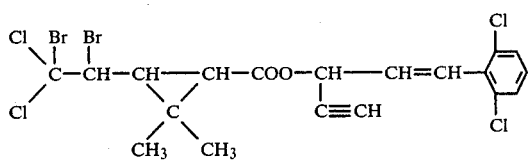

1,4 (m 6H); 1,85-2,85 (m, 3H); 6,05-7,15 (m, 3H); 7,5-8,2 (m, 3H) cis.

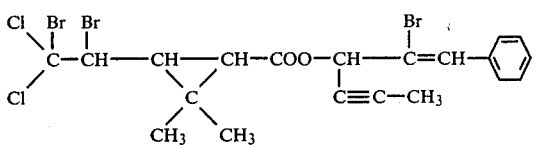

1,35 (m, 6H); 1,75-2,2 (m, 5H); 5,28 (m, 1H); 6,24 (m, 1H); 7,22-7,9 (m, 5H) cis.

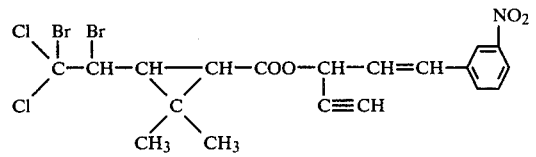

1,35 (m, 6H); 1,8-2,52 (m, 2H); 2,7 (m, 1H); 5,3 (m, 1H); 6,02- 8,45 (m, 7H) cis.

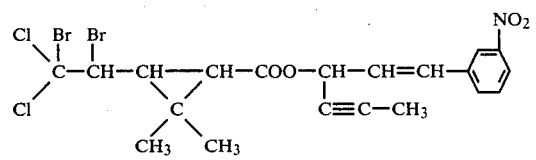

1,35 (m, 6H); 1,75-2,55 (m, 5H); 5,3 (m, 1H); 5,95-8,45 (m, 7H) cis.

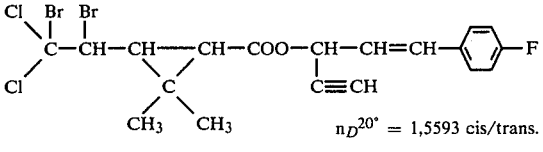

$n_D^{20°} = 1,5593$ cis/trans.

EXAMPLE 2

(A) Insecticidal stomach-poison action

Cotton plants were sprayed with a 0.05% aqueous active-substance emulsion (obtained from a 10% emulsifiable concentrate). After drying of the coating, larvae of *Spodoptera littoralis* in the L3-stage and of *Heliothis virescens* in the L3 stage were placed onto the cotton plants. The test was carried out at 24° C. with 60% relative humidity.

Compounds according to Example 1 exhibited in the above test a good insecticidal stomach-poison action against *Spodoptera littoralis* and *Heliothis virescens* larvae.

EXAMPLE 3

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatographysprayer in a manner ensuring no overflow of the sprayliquor. An assessment was made after 2 and 7 days, by examination under a binocular microscope, of the living larvae and of the dead larvae, adults and eggs, and the results were expressed as percentages. The treated plants were kept during the "holding time" in greenhouse compartments at 25° C.

Compounds according to Example 1 were effective in the above test against adults, larvae and eggs of *Tetranychus urticae*.

EXAMPLE 4

Action against ticks (A) *Rhipcephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

What is claimed is:

1. A cyclopropanecarboxylic acid ester of the formula

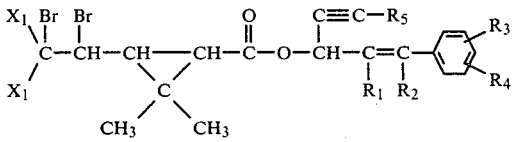

in which
X1 is fluorine, chlorine or bromine,
R1 and R2 are each hydrogen, fluorine, chlorine, bromine or methyl, $R_3$ and $R_4$ are each hydrogen, fluorine, chlorine, bromine, methyl, methoxy, nitro or dimethylamime, or together as methylenedioxy, and $R_5$ is hydrogen or methyl.

2. A compound according to claim 1, wherein $X_1$ is chlorine or bromine, $R_1$ is hydrogen, chlorine, bromine or methyl, $R_2$ is hydrogen, $R_3$ is hydrogen, chlorine, bromine, nitro or dimethylamine, or $R_4$ is hydrogen.

3. A compound according to claim 2, wherein $X_1$ is chlorine, $R_1$ is hydrogen, chlorine or bromine, and, $R_3$, and $R_5$ are each hydrogen.

4. The compound according to claim 3 of the formula

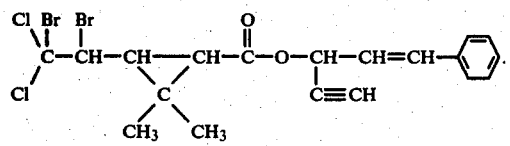

5. The compound according to claim 3 of the formula

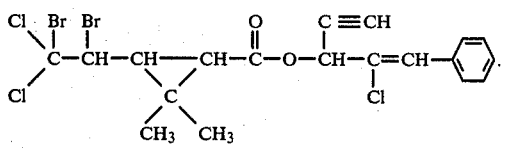

6. The compound according to claim 3 of the formula

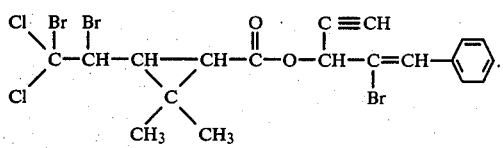

7. An insecticidal and acaricidal composition comprising (1) an insecticidally or acaracidally effective amount of a compound according to claim 1 and (2) a carrier.

8. A method for controlling insects and acarids which comprises applying thereto an insecticidally or acaricidally effective amount of a compound according to claim 1.

9. A method according to claim 8 in which, in the compound, $X_1$ is chlorine or bromine, $R_1$ is hydrogen, chlorine, bromine or methyl, $R_2$ is hydrogen, $R_3$ is hydrogen, chlorine, bromine, nitro or dimethylamino, and $R_4$ is hydrogen.

10. A method according to claim 9 in which, in the compound, $X_1$ is chlorine, $R_1$ is hydrogen, chlorine or bromine, and $R_3$ and $R_5$ are each hydrogen.

* * * * *